(12) United States Patent
Shin et al.

(10) Patent No.: US 11,261,475 B2
(45) Date of Patent: Mar. 1, 2022

(54) NANO-NEUROTOXICITY BIO-MARKER COMPOSITION BASED ON INTRACELLULAR AGGREGATES WHICH ARE BIOMARKERS OF DEGENERATIVE BRAIN DISEASES

(71) Applicant: AJOU UNIVERSITY INDUSTRY-ACADEMIC COOPERATION FOUNDATION, Suwon-si (KR)

(72) Inventors: Tae Hwan Shin, Daegu (KR); Geetika Phukan, Suwon-si (KR); Man Jeong Paik, Seoul (KR); Hyeon-Seong Lee, Incheon (KR); Hyung-Jin Park, Suwon-si (KR); Da Yeon Lee, Ulsan (KR); Gwang Lee, Suwon-si (KR)

(73) Assignee: AJOU UNIVERSITY INDUSTRY-ACADEMIC COOPERATION FOUNDATION

( * ) Notice: Subject to any disclaimer, the term of this patent is extended or adjusted under 35 U.S.C. 154(b) by 510 days.

(21) Appl. No.: 16/311,161

(22) PCT Filed: May 12, 2017

(86) PCT No.: PCT/KR2017/004948
§ 371 (c)(1),
(2) Date: Dec. 18, 2018

(87) PCT Pub. No.: WO2017/222180
PCT Pub. Date: Dec. 28, 2017

(65) Prior Publication Data
US 2019/0194715 A1  Jun. 27, 2019

(30) Foreign Application Priority Data
Jun. 20, 2016 (KR) .................. 10-2016-0076570

(51) Int. Cl.
*C12Q 1/02* (2006.01)
*C12Q 1/6883* (2018.01)
(Continued)

(52) U.S. Cl.
CPC ........... *C12Q 1/025* (2013.01); *C12Q 1/6837* (2013.01); *C12Q 1/6881* (2013.01);
(Continued)

(58) Field of Classification Search
None
See application file for complete search history.

(56) References Cited

U.S. PATENT DOCUMENTS 9,689,019 B2 * 6/2017 Shim .................... C12Q 1/6809
2011/0064739 A1 * 3/2011 Borlak .................... A61P 35/04
424/138.1

(Continued)

FOREIGN PATENT DOCUMENTS

KR    10-2014-0013389 A    2/2014

OTHER PUBLICATIONS

Rao et al, J. Neurochem., vol. 74, pp. 1106-1111, published 2000.*
(Continued)

*Primary Examiner* — Robert T. Crow
(74) *Attorney, Agent, or Firm* — Revolution IP, PLLC

(57) ABSTRACT

A method of assessing neurotoxicity of nanoparticles, includes: preparing a tissue or cell sample of mammal exposed to the nanoparticles; analyzing at least one polyamine metabolite selected from the group consisting of putrescine, N1-acetylspermidine, N8-acetylspermidine, N1-acetylspermine and spermine in the sample; and comparing expression degree of the polyamine metabolite with that of a control.

4 Claims, 2 Drawing Sheets

Specification includes a Sequence Listing.

(51) Int. Cl.
    *C12Q 1/6837* (2018.01)
    *C12Q 1/6881* (2018.01)
(52) U.S. Cl.
    CPC ..... *C12Q 1/6883* (2013.01); *C12Q 2600/106* (2013.01); *C12Q 2600/112* (2013.01); *C12Q 2600/142* (2013.01); *C12Q 2600/156* (2013.01); *C12Q 2600/158* (2013.01); *C12Q 2600/16* (2013.01)

(56) References Cited

U.S. PATENT DOCUMENTS

| | | | |
|---|---|---|---|
| 2014/0024545 A1 | 1/2014 | Shim et al. | |
| 2014/0154725 A1* | 6/2014 | Aadal Nielsen ... | G01N 33/5058 435/29 |
| 2015/0118218 A1* | 4/2015 | Travis .................. | C12Q 1/32 424/94.64 |

OTHER PUBLICATIONS

Lasbury et al, J. Biol. Chem, vol. 282, p. 11009-11020, published Feb. 21, 2007.*

Shin et al (Stem Cells International, vol. 2016, pp. 1-11, published Jun. 16, 2016).*

Zahedi et al, J. Neurotrauma, vol. 27, pp. 515-525, published Mar. 2010.*

International Search Report for PCT/KR2017/004948 dated Sep. 12, 2017 from Korean Intellectual Property Office.

Cervelli et al., "A New Transgenic Mouse Model for Studying the Neurotoxicity of Spermine Oxidase Dosage in the Response to Excitotoxic Injury", PLOS ONE, vol. 8, No. 6, document No. e64810 (Jun. 2013).

Wang et al., "Spermidine on neurodegenerative diseases", Cell Cycle, vol. 14, No. 5, pp. 697-698 (Mar. 1, 2015).

Shim et al., "Analysis of Changes in Gene Expression and Metabolic Profiles Induced by Silica-Coated Magnetic Nanoparticles", ACS Nano, vol. 6, No. 9, pp. 7665-7680 (2012).

Paik et al., "Polyamine patterns in the cerebrospinal fluid of patients with Parkinson's disease and multiple system atrophy", Clinica Chimica Acta, vol. 411, pp. 1532-1535 (2010).

Phukan et al., "Silica-coated magnetic nanoparticles impair proteasome activity and increase the formation of cytoplasmic inclusion bodies in vitro", Scientific Reports, vol. 6, document No. 29095; pp. 1-12 (Jul. 5, 2016).

* cited by examiner

[FIG. 1]
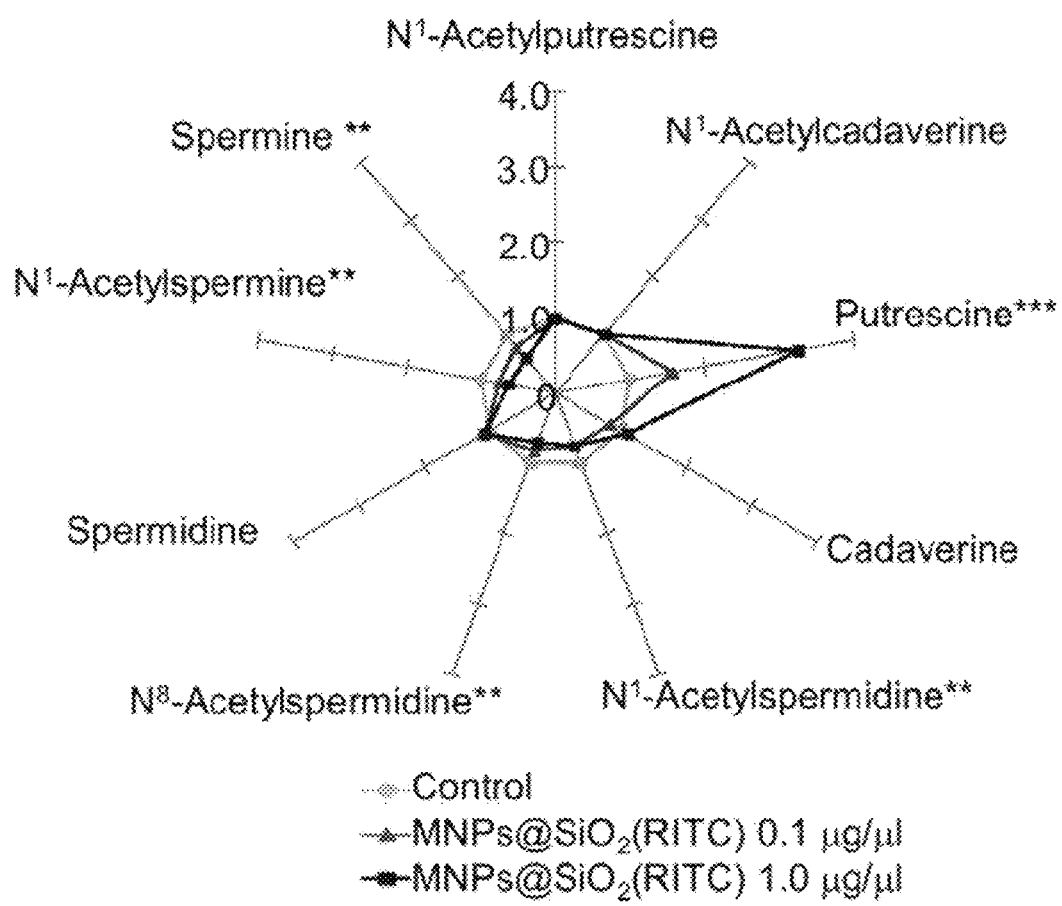

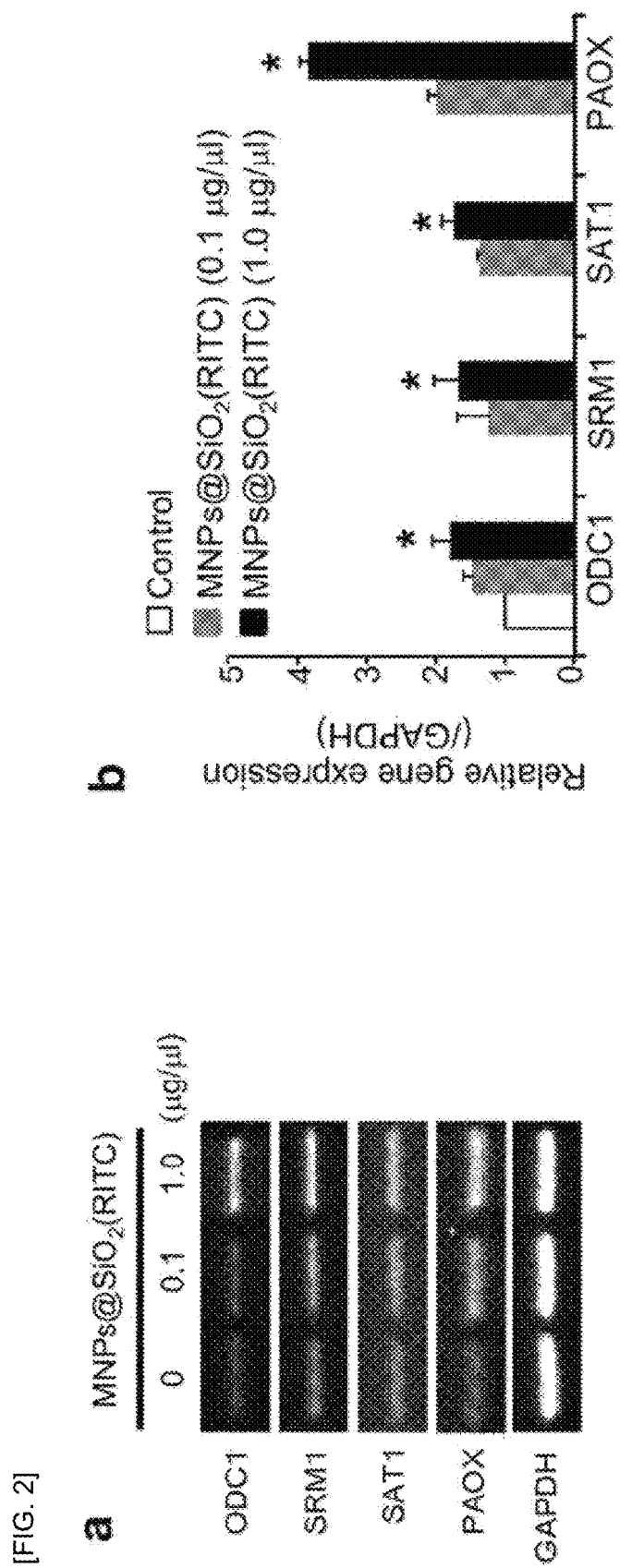
[FIG. 2]

NANO-NEUROTOXICITY BIO-MARKER COMPOSITION BASED ON INTRACELLULAR AGGREGATES WHICH ARE BIOMARKERS OF DEGENERATIVE BRAIN DISEASES

TECHNICAL FIELD

The present invention relates to a biomarker composition for diagnosing the neurotoxicity of nanoparticles, a microarray chip for diagnosing the neurotoxicity of nanoparticles comprising the same, and a method of evaluating the neurotoxicity of nanoparticles using the same.

BACKGROUND ART

The nanotechnology is developing in various fields for not only the industrial use of nanomaterials but also medical and research purposes. Accordingly, in addition to workers producing nanomaterials, the public is also increasingly exposed to and contacting nanomaterials.

However, although nanotechnology offers many advantages and benefits enough to be perceived as a new technological revolution throughout the industry, while it is also a well-known fact that it has these potential risks, which can be attributed to the characteristics of nanotechnology.

Namely, the smaller the particle, the larger the ratio of specific surface area, and these small particles having a large specific surface area ratio have increased toxicity when reacted with biological tissue. It has already been revealed that when some nanoparticles such as titanium dioxide, carbon powder, diesel particle, etc. have the smaller size, it becomes more toxic including causing inflammation through academic experiments. In addition, ultrafine nanoparticles may penetrate deep into the alveoli, or migrate to the brain without being filtered on the airways or mucous membranes, and more recently, theories have been reported that nanoparticles can accumulate in the body and cause diseases or central nervous disorders.

However, research on nano-neurotoxicity by nanoparticles is still at an early stage, but it is predicted that risk for potential toxicity to nano-neurotoxicity is increased socially. The smaller the nanoparticles, the larger the specific surface area ratio and these small particles having a large specific surface area ratio have an increased toxicity when reacted with living tissues. However, the harmfulness of the nanoparticles is not well identified in neurons yet.

At present, there are efforts to establish an index of nano-toxicity evaluation internationally, but it is expected that the nano-neurotoxicity biomarker actively develops in the future even though it is still based on the conventional chemical toxicity law.

DISCLOSURE

Technical Problem

In order to solve the above problems, the present invention provides a biomarker composition for diagnosing neurotoxicity of nanoparticles comprising polyamine metabolites.

Also, the present invention provides a composition for diagnosing neurotoxicity of nanoparticles comprising an agent for detecting a polyamine metabolite.

In addition, the present invention provides a microarray chip for diagnosing neurotoxicity of nanoparticles in which all nucleic acid sequences of genes of at least one polyamine metabolites selected from the group consisting of putrescine, $N^1$-acetylspermidine, $N^8$-acetylspermidine, $N^1$-acetylspermine and spermine; or an oligonucleotide which is a fragment of the gene; or a complementary strand molecule thereof, is integrated.

Furthermore, the present invention provides a method of assessing neurotoxicity of nanoparticles comprising: preparing a tissue or cell sample of mammal exposed to the nanoparticle; analyzing at least one polyamine metabolite selected from the group consisting of putrescine, $N^1$-acetylspermidine, $N^8$-acetylspermidine, $N^1$-acetylspermine and spermine in the sample; and comparing expression degree of the polyamine metabolite with that of a control.

In addition, the present invention provides a biomarker composition for diagnosing neurotoxicity of nanoparticles comprising at least one gene selected from the group consisting of ODC1 (gene registration number: NM_002539), SAT1 (gene registration number: NM_002970), PAOX (gene registration number: NM_152911) and SRM1 (gene registration number: NM_003132).

Further, the present invention provides a composition for diagnosing neurotoxicity of nanoparticles comprising an agent for detecting at least one gene selected from the group consisting of ODC1 (gene registration number: NM_002539), SAT1 (gene registration number: NM_002970), PAOX (gene registration number: NM_152911) and SRM1 (gene registration number: NM_003132).

Further, the present invention provides a microarray chip for diagnosis of nanoparticle neurotoxicity in which all nucleic acid sequences of at least one genes selected from the group consisting of ODC1 (gene registration number: NM_002539), SAT1 (gene registration number: NM_002970), PAOX (gene registration number: NM_152911) and SRM1 (gene registration number: NM_003132); or an oligonucleotide which is a fragment of the gene; or a complementary strand molecule thereof, is integrated.

Further, the present invention provides a method of assessing neurotoxicity of nanoparticles comprising: preparing a tissue or cell sample of mammal exposed to the nanoparticle; analyzing at least one genes selected from the group consisting of ODC1 (gene registration number: NM_002539), SAT1 (gene registration number: NM_002970), PAOX (gene registration number: NM_152911) and SRM1 (gene registration number: NM_003132) in the sample; and comparing expression degree of the gene with that of a control.

Advantageous Effects

According to the present invention, nanoparticles such as MNPs@$SiO_2$ (RITC) increase putrescine and reduce spermidine and spermine, which are the intracellular polyamine metabolites, and also increases the expression of ODC1, SAT1, PAOX and SRM1 which are genes involved in the metabolism of polyamines, and thus increases the inclusion body formation and induces neurodegeneration. As an index for determining the nano-neurotoxicity through formation of intracellular aggregates by nanoparticles, nano-neurotoxicity indicators can be provided using gene associated with polyamine metabolites and polyamine metabolism.

DESCRIPTION OF DRAWINGS

FIG. 1 shows the results of quantitative analysis of polyamines by GC/MS in the nerve cell line SH-SY5Y cells treated with MNPs@$SiO_2$ (RITC).

FIG. 2 shows the results of polyamine metabolism-related gene expression analysis in nerve cell line SH-SY5Y cells treated with MNPs@SiO$_2$ (RITC) and in which a indicates RT-PCR and b indicates real-time PCR.

BEST MODE

The inventors of the present invention have researched to evaluate neurotoxicity caused by exposure of nanoparticles, and confirmed that the polyamine metabolite and related gene expression have changed in nerve cells upon treatment with nanoparticles of a certain concentration or higher and it can be used as an indicator of neurotoxicity of nanoparticles, and they completed the present invention.

Therefore, the present invention provides a biomarker composition for diagnosing neurotoxicity of nanoparticles comprising polyamine metabolites.

Also, the present invention provides a composition for diagnosing neurotoxicity of nanoparticles comprising an agent for detecting a polyamine metabolite.

The polyamine metabolite may be at least one selected from the group consisting of putrescine, N$^1$-acetylspermidine, N$^8$-acetylspermidine, N$^1$-acetylspermine and spermine.

In addition, the present invention provides a microarray chip for diagnosing neurotoxicity of nanoparticles in which all nucleic acid sequences of genes of at least one polyamine metabolites selected from the group consisting of putrescine, N$^1$-acetylspermidine, N$^8$-acetylspermidine, N$^1$-acetylspermine and spermine; or an oligonucleotide which is a fragment of the gene; or a complementary strand molecule thereof, is integrated.

Furthermore, the present invention provides a method of assessing neurotoxicity of nanoparticles comprising: preparing a tissue or cell sample of mammal exposed to the nanoparticle; analyzing at least one polyamine metabolite selected from the group consisting of putrescine, N$^1$-acetylspermidine, N$^8$-acetylspermidine, N$^1$-acetylspermine and spermine in the sample; and comparing expression degree of the polyamine metabolite with that of a control.

The analysis is to quantitatively analyze polyamine metabolites by GC/MS analysis and the like, and that the expression of putrescine is increased and N$^1$-acetylspermidine, N$^8$-acetylspermidine, N$^1$-acetylspermine and spermine are decreased, can be concluded that nanoparticles induce neurotoxicity by increasing the formation of inclusion body in nerve cells. Particularly, the increase of the metabolite can mean a state where the expression level of the control group is at least twice the normal expression level of the control group not treated with the nanoparticles, and the decrease of the metabolite can mean equal to or less than ½ times of the normal expression level of the control group not treated with the nanoparticles.

Also, the present invention provides a biomarker composition for diagnosing neurotoxicity of nanoparticles comprising at least one gene selected from the group consisting of ODC1 (gene registration number: NM_002539), SAT1 (gene registration number: NM_002970), PAOX (gene registration number: NM_152911) and SRM1 (gene registration number: NM_003132).

In addition, the present invention provides a composition for diagnosing neurotoxicity of nanoparticles comprising an agent for detecting at least one gene selected from the group consisting of ODC1 (gene registration number: NM_002539), SAT1 (gene registration number: NM_002970), PAOX (gene registration number: NM_152911) and SRM1 (gene registration number: NM_003132).

Furthermore, the present invention provides a microarray chip for diagnosis of nanoparticle neurotoxicity in which all nucleic acid sequences of at least one genes selected from the group consisting of ODC1 (gene registration number: NM_002539), SAT1 (gene registration number: NM_002970), PAOX (gene registration number: NM_152911) and SRM1 (gene registration number: NM_003132); or an oligonucleotide which is a fragment of the gene; or a complementary strand molecule thereof, is integrated.

In addition, the present invention provides a method of assessing neurotoxicity of nanoparticles comprising: preparing a tissue or cell sample of mammal exposed to the nanoparticle; analyzing at least one genes selected from the group consisting of ODC1 (gene registration number: NM_002539), SAT1 (gene registration number: NM_002970), PAOX (gene registration number: NM_152911) and SRM1 (gene registration number: NM_003132) in the sample; and comparing expression degree of the gene with that of a control.

The above analysis is for analyzing the expression level of the gene by RT-PCR or real-time PCR, etc. and if the expression of ODC1 (gene registration number: NM_002539), SAT1 (gene registration number: NM_002970), PAOX (gene registration number: NM_152911) and SRM1 (gene registration number: NM_003132) is increased, it can be judged that the nanoparticles increased the formation of inclusion bodies in the nerve cells, leading to neurotoxicity. Particularly, the expression increase in these genes may mean a state in which the expression level of the gene is two times or more the normal expression level of the control group which is not treated with the nanoparticles.

In one embodiment of the present invention, the nanoparticles may be all nanoparticles having increased neurotoxicity upon reacting with living tissues, more specifically nanoparticles in the air, nanoparticles contained in a cosmetic composition, nanoparticles contained in a pharmaceutical composition, semiconductor nanoparticles, and the like, but it is not limited thereto. In addition, the nanoparticles may also be in the form of a core-shell, and the shell may include silica, but it is not limited thereto.

The microarray chip according to the present invention can be manufactured by a method known to those skilled in the art. A method of fabricating the microarray chip is as follows. In order to immobilize the searched protein or gene biomarker as a probe DNA molecule on a substrate of a DNA chip, it is preferred to use a micropipetting method using a piezoelectric method or a method using a pin type spotter, or the like, but it is not limited thereto. The substrate of the DNA microarray chip is preferably coated with one active group selected from the group consisting of aminosilane, poly-L-lysine and aldehyde, but it is not limited thereto. The substrate may be selected from the group consisting of slide glass, plastics, metal, silicone, nylon film and nitrocellulose film, but it is not limited thereto.

In addition, the present invention provides a kit for diagnosing neurotoxicity of nanoparticles comprising the microarray chip.

In addition, the kit may further include a fluorescent material, and the fluorescent material may be selected from the group consisting of strepavidin-like phosphatase conjugate, a chemiflurorensce and a chemiluminescent substance, but it is not limited thereto.

Furthermore, the kit may further comprise a reaction reagent and the reaction reagent may include a buffer solution used for hybridization, a reverse transcriptase for synthesizing cDNA from RNA, cNTPs and rNTP (pre-mixed or separated feed type), a labeling reagent such as a chemical inducer of a fluorescent dye, or a washing buffer solution, but it is not limited thereto and may include reaction reagents necessary for hybridization of a DNA microarray chip known to those skilled in the art.

Also, the present invention provides a kit for diagnosing neurotoxicity of nanoparticles which are complementary to the biomarker gene and comprise a pair of primers capable of amplifying a biomarker gene.

As pair of primers, both forward and reverse primer pairs having a length of 15 to 50-mer, which is designed so that the amplification product of the biomarker gene is 100 to 300 bp, are can be used. In addition, the kit may further comprise a reaction reagent and the reaction reagent may include a reverse transcriptase for synthesizing cDNA from RNA, cNTPs and rNTP (pre-mixed or separated feed type), a labeling reagent such as a chemical inducer of a fluorescent dye, or a washing buffer solution, but it is not limited thereto and may include reaction reagents necessary for RT-PCR reaction known to those skilled in the art.

According to one specific embodiment of the present invention, the neurotoxicity of the nanoparticles can be evaluated by a method comprising: 1) separating RNA from a tissue or cell sample of a mammal exposed to nanoparticles as an experimental group; 2) labeling the experimental group and the control group with different fluorescent substances while synthesizing the RNA of the experimental group and the control group of the step 1) with cDNA; 3) hybridizing the cDNA labeled with different fluorescent substances of the step 2) with the microarray chip according to the present invention; 4) analyzing the DNA microarray chip reacted in the step 3); and 5) comparing the expression level of the marker gene of the experimental group with that of the control group in the data analyzed in the step 4).

According to another embodiment of the present invention, the neurotoxicity of the nanoparticles can be evaluated by a method comprising: 1) separating RNA from a tissue or cell sample of a mammal exposed to nanoparticles as an experimental group; 2) performing real-time reverse transcriptase polymerase chain reaction (RT-PCR) using a pair of primers complementary to the biomarker gene and capable of amplifying the biomarker gene of the present invention as for RNA of the experimental group and the control group of the step 1); and 3) comparing and confirming the amount of the gene product of the step 2) with that of the control.

Hereinafter, the present invention will be described in detail with reference to the following examples. It should be noted, however, that the following examples are illustrative of the present invention and are not intended to limit the scope of the present invention. Embodiments of the present invention are provided to more fully describe the present invention to those skilled in the art.

<Example 1> Cell Culture and MNPs@SiO$_2$ (RITC) Treatment

1. Cell Culture

Human nerve cell SH-SY5Y cells were purchased from ATCC and cultured in Dulbecco's modified Eagle's medium (DMEM, Gibco, USA) containing 10% fetal bovine serum (FBS, Gibco, USA), 100 units/ml penicillin and 100 μg/mL streptomycin (Gibco, USA). Cells were incubated at 37° C. and under 5% humidity and CO$_2$ atmospheric conditions.

2. MNPs@SiO$_2$ (RITC) Particle Preparation and Cell Treatment

The MNPs@SiO$_2$ (RITC) particles were prepared according to a known method (Angew Chem Int Ed Engl 44, 1068-1071, 2005) using CoFe$_2$O$_3$ as the core and silica as the shell, and chemically bonding with the rhodamine isothiocyanate dye.

SH-SY5Y cells were treated with 0.1 and 1.0 μg/μl of MNPs@SiO$_2$ (RITC) for 12 hours, respectively.

<Example 2> Gas Chromatography-Mass Spectrometry (GC/MS Analysis)

GC/MS analysis was performed for polyamine analysis in cells treated with MNPs@SiO$_2$ (RITC). The GC-MS analysis was performed using Agilent 6890 gas chromatograph and Agilent 5973 mass-selective detector (70 eV, electron impact mode) as an interface and Ultra-2 (5% phenyl-95% methylpolysiloxane bonded phase; 25 m×0.20 mm i.d., 0.11 μm film thickness) cross-coupled capillary column (Agilent Technologies, USA). The injector, interface, and ion feed were at 260, 300 and 230° C., respectively. A constant flow rate of 0.5 mL/min of helium was used as the mobile gas and the sample was injected in a split-injection mode (10:1).

The temperature for the analysis of the polyamines (putrescine, spermidine, spermine, $N^1$-acetylputrescine, $N^1$-acetylcadaverine, $N^1$-acetylspermidine, $N^8$-acetylspermidine, $N^1$-acetylspermine, and cadaverine) was set at 140° C. for the initial 2 minutes and then the temperature was raised to 240° C. at a rate of 5° C./min and then to 300° C. at a rate of 30° C./min and maintained for 3 minutes. The mass range was 50-600 u and the scan speed was set at 0.99 scans/s.

As shown in FIG. 1, when the nanoparticles were treated at a high concentration (1.0 μg/μl), putrescine was increased by about 300% and $N^1$-acetylspermidine, $N^8$-acetylspermidine, $N^1$-acetylspermine and spermine were decreased by 30%.

<Example 3> Analysis of Polyamine Metabolism Related Gene Expression

1. Preparation of Total RNA Sample

RNA from cells treated with MNPs@SiO$_2$ (RITC) or not treated was isolated using RNAZOL® B (Tel-Test, Inc., USA) and purified using RNeasy Mini Kit (Qiagen, USA). More specifically, 2×10$^6$ cells were obtained by treating with 500 μl of RNAZOL® B solution, followed by addition of 70 μl of chloroform and incubation at 4° C. for 5 minutes. Cells were treated with 600 μl of isopropyl alcohol to precipitate RNA, the RNA pellet was washed with 70% ethanol and air dried, and RNA was eluted from the pellet using RNase-free water (WelGene, Korea). The purity of the RNA was quantitated by a spectrophotometer (Eppendorf, USA). The purity of the RNA used in the PCR experiments was 1.8-2.0 based on optical density (OD) 260/230 and 260/280.

2. Gene Expression Analysis

To quantify gene expression, total RNA samples were reverse transcribed using RealMOD™ SYBR Green Real-time PCR kit (iNtRON Biotechnology, Seongnam, Korea) and amplified using primers appropriate for each fragment. The reaction was carried out at 5° C. for 2 minutes, at 95° C. for 30 seconds, then at 95° C. for 5 seconds and at 53° C. for 30 seconds. PCR products were analyzed by forming melting curves using a MJ Opticon Monitor Version 3.1 (Bio-Rad, Hercules, Calif.).

TABLE 1

| Gene name | Symbol | NCBI Ref Seq | Direction | Primer sequence (5'-3') |
|---|---|---|---|---|
| *Homo sapiens* ornithine decarboxylase 1 | ODC1 | NM_002539 | Forward | GAG CCC GGC AGA TAC TAT GT (Sequence 1) |
| | | | Reverse | GCT TTA CAT GTG CGT GGT CA (Sequence 2) |
| *Homo sapiens* spermidine synthase 1 | SRM1 | NM_003132 | Forward | CGA AAG GTG CTG ATC ATC GG (Sequence 3) |
| | | | Reverse | CAA AAC CGT CAC CCA CAT GT (Sequence 4) |
| *Homo sapiens* spermidine/spermine acetyltransferase 1 | SAT1 | NM_002970 | Forward | ACC TAT GAC CCG TGG ATT GG (Sequence 5) |
| | | | Reverse | TGC TAC CAA GAA GTG CAT GC (Sequence 6) |
| *Homo sapiens* polyamine oxidase | PAOX | NM_152911 | Forward | CAA GAA GGA GAT TGG CCA GC (Sequence 7) |
| | | | Reverse | CAG CAC GGT ATA CTC CCC AA (Sequence 8) |
| *Homo sapiens* glyceraldehyde 3-phosphate dehydrogenase | GAPDH | NM_002046 | Forward | GAA GAC TGT GGA TGG CCC (Sequence 9) |
| | | | Reverse | CCA TGC CAG TGA GCT TCC (Sequence 10) |

Referring to Table 1 and FIG. 2, the expression of ODC1, SAT1, PAOX and SRM1 genes was increased, and the expression of SRM1 gene was not relatively higher than that of other genes.

Treatment of high concentration (1.0 μg/μL) of nanoparticles can induce changes in the expression of polyamine metabolites and related genes, and high concentrations of nanoparticles can affect the living body in terms of genetic and metabolism aspects. The present invention provides a method of clearly evaluating the nanoparticles under a present situation that a clear methodological guideline or biological indicators for evaluating the safety of nanoparticles are not standardized.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A method of assessing neurotoxicity of nanoparticles comprising:
   preparing a tissue or cell sample of mammal;
   treating the tissue or cell sample with the nanoparticles;
   analyzing polyamine metabolites including putrescine, N1-acetylspermidine, N8-acetylspermidine, N1-acetylspermine and spermine in the sample;
   comparing an amount of the polyamine metabolites with that of a control; and
   determining the neurotoxicity of nanoparticles of the sample, if:
      an amount of the putrescine is increased at least twice compared to the control not treated with the nanoparticles; and
      an amount of the N1-acetylspermidine, the N8-acetylspermidine, the N1-acetylspermine and the spermine is decreased less than ½ times compared to the control not treated with the nanoparticles.

2. The method of assessing neurotoxicity of nanoparticles of claim 1, further comprising:
   analyzing at least one gene selected from the group consisting of ornithine decarboxylase 1 (ODC1), spermidine/spermine N1 acetyltransferase 1 (SAT1), polyamine oxidase (PAOX) and spermidine synthase 1 (SRM1) in the sample, wherein the at least one gene is involved in polyamine metabolism; and
   comparing expression degree of the gene with that of a control.

3. The method of assessing neurotoxicity of nanoparticles of claim 2,
   wherein the sample is exposed to the nanoparticles if an expression of the ODC1 gene, the SAT1 gene, the PAOX gene and the SRM1 gene is increased compared to the control not treated with the nanoparticles.

4. The method of assessing neurotoxicity of nanoparticles of claim 1, wherein the nanoparticles are MNPs@SiO$_2$ (RITC) particles.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Forward primer for ODC1

<400> SEQUENCE: 1
gagcccggca gatactatgt         20

<210> SEQ ID NO 2
<211> LENGTH: 20
<212> TYPE: DNA
<213> ORGANISM: Artificial Sequence
<220> FEATURE:
<223> OTHER INFORMATION: Reverse primer for ODC1

<400> SEQUENCE: 2
gctttacatg tgcgtggtca         20

<210> SEQ ID NO 3
<211> LENGTH: 20
<212> TYPE: DNA
<213> ORGANISM: Artificial Sequence
<220> FEATURE:
<223> OTHER INFORMATION: Forward primer for SRM1

```
<400> SEQUENCE: 3
cgaaaggtgc tgatcatcgg                                          20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for SRM1

<400> SEQUENCE: 4
caaaaccgtc acccacatgt                                          20

<210> SEQ ID NO 5
<211> LENGTH: 20
<212> TYPE: DNA
<213> ORGANISM: Artificial Sequence
<220> FEATURE:
<223> OTHER INFORMATION: Forward primer for SAT1

<400> SEQUENCE: 5
acctatgacc cgtggattgg                                          20

<210> SEQ ID NO 6
<211> LENGTH: 20
<212> TYPE: DNA
<213> ORGANISM: Artificial Sequence
<220> FEATURE:
<223> OTHER INFORMATION: Reverse primer for SAT1

<400> SEQUENCE: 6
tgctaccaag aagtgcatgc                                          20

<210> SEQ ID NO 7
<211> LENGTH: 20
<212> TYPE: DNA
<213> ORGANISM: Artificial Sequence
<220> FEATURE:
<223> OTHER INFORMATION: Forward primer for PAOX

<400> SEQUENCE: 7
caagaaggag attggccagc                                          20

<210> SEQ ID NO 8
<211> LENGTH: 20
<212> TYPE: DNA
<213> ORGANISM: Artificial Sequence
<220> FEATURE:
<223> OTHER INFORMATION: Reverse primer for PAOX

<400> SEQUENCE: 8
cagcacggta tactccccaa                                          20

<210> SEQ ID NO 9
<211> LENGTH: 18
<212> TYPE: DNA
<213> ORGANISM: Artificial Sequence
<220> FEATURE:
<223> OTHER INFORMATION: Forward primer for GAPDH

<400> SEQUENCE: 9
gaagactgtg gatggccc                                            18

<210> SEQ ID NO 10
```

```
<211> LENGTH: 18
<212> TYPE: DNA
<213> ORGANISM: Artificial Sequence
<220> FEATURE:
<223> OTHER INFORMATION: Reverse primer for GAPDH

<400> SEQUENCE: 10
ccatgccagt gagcttcc                                                      18
```